United States Patent [19]

Wachtel et al.

[11] Patent Number: 4,857,298

[45] Date of Patent: Aug. 15, 1989

[54] I*-DIAGNOSTICS FOR MONOAMINE RECEPTORS USING ERGOLINES

[75] Inventors: Helmut Wachtel; Herbert H. Schneider; Peter-Andreas Löschmann; Rainer Dorow; Reinhard Horowski; Bernard Acksteiner; Paul-Eberhard Schulze; Gerhard Sauer, all of Berlin, Fed. Rep. of Germany

[73] Assignee: Schering Aktiengesellschaft, Berlin and Bergkamen, Fed. Rep. of Germany

[21] Appl. No.: 72,090

[22] Filed: Jul. 10, 1987

[30] Foreign Application Priority Data

Jul. 10, 1986 [DE] Fed. Rep. of Germany ....... 3623438

[51] Int. Cl.⁴ ..................... A61K 49/02; C07D 457/12
[52] U.S. Cl. ....................................... 424/1.1; 546/68; 514/288
[58] Field of Search ..................... 546/67, 68; 424/1.1; 514/288

[56] References Cited

U.S. PATENT DOCUMENTS

| | | | |
|---|---|---|---|
| 3,920,664 | 11/1975 | Clemens et al. | 546/68 X |
| 3,959,288 | 5/1976 | Bach et al. | 546/67 |
| 4,054,660 | 10/1977 | Clemens et al. | 514/288 |
| 4,199,579 | 4/1980 | Ferrari et al. | 514/288 X |
| 4,299,836 | 11/1981 | Mago nee Karacsony et al. | 514/288 |
| 4,417,051 | 11/1983 | Sauer | 546/67 |
| 4,695,635 | 9/1987 | Sauer et al. | 546/67 |

FOREIGN PATENT DOCUMENTS

| | | | |
|---|---|---|---|
| 0056358 | 7/1982 | European Pat. Off. | 514/288 |
| 3247514 | 6/1984 | Fed. Rep. of Germany | 514/288 |

OTHER PUBLICATIONS

Maziere et al, "[$^{76}$Br] Bromolisuride: A New Tool for Quantitative in vivo Imaging", Eur. J. Pharmalol, 8/1986, 127(3), 239-47 [C.A. 105:187032p].

Maziere et al., "[$^{76}$Br] Bromolisuride: A New Radiopharmaceutical for in vivo Studies", J. Biophys. Biomec. 9/15/86, 10(2 Supp.), 25-6, [C.A. 106:15362a].

H. F. Kung et al., "Synthesis of New Bis(aminoethanethiol) (BAT) Derivatives: Possible Ligands for Tc Brain Damaging Agents", 1985 American Chemical Society, pp. 1280-1284.

H. F. Kung et al., "Synthesis and Biodistribution of Neutral Lipid-Soluble Complexes that Cross the Blood-Brain Barrier, Journal of Nuclear Medicine", Mar. 1984, vol. 25, No. 3, pp. 326-332.

Primary Examiner—John S. Maples
Attorney, Agent, or Firm—Millen, White & Zelano

[57] ABSTRACT

Compounds of general Formula I labeled with $^{121}$I, $^{122}$I, $^{123}$I, $^{124}$I, $^{125}$I, $^{131}$I and $^{132}$I isotopes

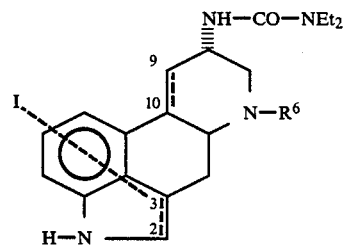

wherein
$R^6$ is a $C_{1-6}$ aliphatic hydrocarbon residue and
$C_2$–$C_3$, $C_9$–$C_{10}$ is a single or a double bond, as well as their acid addition salts,
are useful as diagnostic media, e.g., in imaging dopamine and other receptors.

31 Claims, No Drawings

I*-DIAGNOSTICS FOR MONOAMINE RECEPTORS USING ERGOLINES

CROSS-REFERENCE TO RELATED APPLICATION

This application is related to application Ser. No. 07/07/944, now abandoned, which disclosure is incorporated by reference herein.

BACKGROUND OF THE INVENTION

This invention relates to ergolinylurea derivatives containing radioactive iodine, their preparation, and their use as diagnostic agents.

SUMMARY OF THE INVENTION

It is an object of this invention to provide new compounds valuable as diagnostics.

Upon further study of the specification and appended claims, further objects and advantages of this invention will become apparent to those skilled in the art.

These objects have been achieved by providing new compounds of Formula I

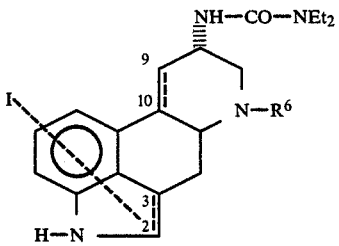

wherein
$R^6$ is a $C_{1-6}$ hydrocarbon residue and $C_2$–$C_3$ and $C_9$–$C_{10}$ each independently represent a single or double bond,
as well as their acid addition salts.

Suitable hydrocarbon residues $R^6$ include straight chained, branched, saturated, unsaturated, acyclic or cycloaliphatic groups of up to 6 carbon atoms. Hydrocarbon residues of 1–4 carbon atoms are preferred, for example, methyl ethyl, n-propyl, isopropyl, butyl, cyclopropylmethyl, 2-propenyl, allyl, etc. Thus, generally suitable groups are alkyl, alkenyl, alkynyl, each of these groups optionally substituted by a cycloalkyl group, or cycloalkyl, cycloalkenyl, cycloalkynyl, etc.

When $C_9$–$C_{10}$ represents a single bond, the hydrogen atom in the 10-position is of the α-configuration.

In the compounds of this invention, typically there are from 1–2 radioactive iodine atoms, preferably only a single radioactive iodine atom.

Suitable iodine isotopes I* are, for example, the $^{121}I$, $^{122}I$, $^{123}I$, $^{124}I$, $^{125}I$, $^{131}I$ and $^{132}I$ isotopes.

Autoradiography and, in particular, positron emission tomography (PET) and single-photon emission computer tomography (SPECT) are suitable for the detection of functional and structural cerebral changes. Since cerebral functions are organized topographically, and no conclusion can be drawn from the functional condition of a cell or a united cell structure—as, for example, in case of the liver—with respect to the function of the entire organ, visualization and quantification of the spatial and chronological distribution of morphological and functional tissue parameters represent an improvement in diagnostics.

It is known that ergolinylurea derivatives affect noradrenergic, dopaminergic and serotoninergic neurons; by binding to the presynaptic or postsynaptic neuronal receptors, the activity of the natural neurotransmitter is imitated (agonist) or the activity of the natural neurotransmitter is counteracted (antagonist). It is furthermore known that imaging of dopamine receptors is possible by PET using dopamine antagonistss that emit positrons (Maziere, B., et al., Life Sci. 35: 1349, 1984).

It has now been discovered that the compounds of this invention, on account of their affinity to monoamine receptors, are especially well suited for diagnostic purposes. They can be utilized for the in vivo and in vitro imaging of dopaminergic and other monoaminergic systems and thus are suitable for the visualization of structure and function of dopaminergic and other monoaminergic systems in organisms or parts thereof, such as, for example, the entire brain, basal ganglia, frontal brain, etc.

Diagnostically, recognition of early or advanced cases of Parkinson's disease is possible from an observed lesser enrichment, as compared to a conventional standard, of the labeled dopamine receptor antagonists, such as, for example, radioactively labeled 2-iodo*lisuride, in the basal ganglia; by previous administration of D-2-antagonists, image representation is prevented, showing the efficiency of this invention in imaging central dopamine receptors. Since there is no binding to serotonin receptors, and enrichment takes place within a very brief time period so that radiation stress is low, the compounds of this invention, particularly radioactively labeled 2-I*lisuride, are especially suitable for the selective imaging of central dopamine receptors.

However, it is likewise possible to identify disorders due to lack of dopamine, or disturbances of the dopamine system, such as, for example, in each case of senile dementia, motor hypo-, dys-, or hyperfunction, including late consequences of medicament ingestion, again by reference to a standard image. Furthermore, it is also possible to differentiate, with respect to forms and symptoms, disturbances of the limbic and cortical dopaminergic systems. This is especially valuable, for example, in the field of psychoses and especially in schizophrenias, thus making them accessible to differentiated therapy and therapy control. Dopamine receptors are also found in the hypophysis so that imaging of prolactinomas and their metastases is also possible. The compounds of this invention thus can likewise be employed for the imaging, detection and diagnosis of tumors and metastases.

Thus, the compounds of this invention can be used in a method for imaging dopamine receptors, e.g., using one of the conventional methods mentioned above, typically to determine the level of natural dopamine neurotransmitter function, inter alia. The method can be carried out analogously to the known method with other agents, e.g., as disclosed in H. F. Kung et al., J. of Med. Chem. 1985, 28, 1280 and H. F. Kung et al., J. Nucl. Med. 25; 325-332, 1984. Typically, the compounds are administered parenterally (but also possibly enterally) in the form of their water soluble salts or in a conventional buffer solution. The mixture administered contains the compounds typically in a concentration of 0.01–2 nmoles/ml. Typical dosages are 0.001–10 μg/kg administered 5–15 minutes prior to the first imaging step.

Suitable formulations are those known for the underlying therapeutic agents per se. See, e.g., ethanol-propanediol-saline or ethanol-saline, after sterile filtration of the HPLC-separated compound.

A further advantage of the compounds of this invention is that labeling is effected on known therapeutics by substitution on them with radioactive iodine, thus obtaining in very good yields compounds having a very high specific activity, these compounds likewise being known as therapeutics in the unlabeled condition.

The compounds of this invention can be prepared by a process wherein a compound of Formula II

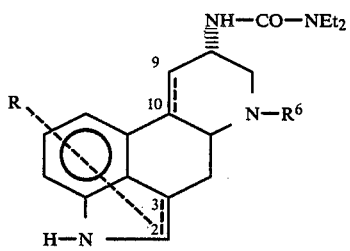

wherein $C_2$–$C_3$, $C_9$–$C_{10}$ and $R^6$ have the meanings given above and

R is hydrogen, iodine or a $C_{1-4}$-alkylsilyl group, (a) if R is hydrogen and $C_2$–$C_3$ is a double bond, are reacted in the presence of an oxidizing agent with Na-[$^{121}$I, $^{122}$I, $^{123}$I, $^{124}$I, $^{125}$I, $^{131}$I or $^{132}$I] iodide; or (b) if R is iodine, are reached with Na[$^{121}$I, $^{122}$I, $^{123}$I, $^{124}$I, $^{125}$I, $^{131}$I or $^{132}$I] iodide; or (c) if R is $C_{1-4}$-alkylsilyl, are reacted with iodine which is labeled with $^{122}$I, $^{123}$I, $^{124}$I, $^{125}$I, $^{131}$I or $^{132}$I isotopes.

For example, the compounds of general Formula I can be produced by reacting the uniodinated compound with radioactively labeled sodium-[I*] iodide in the presence of an oxidizing agent. Suitable oxidizing agents are, for example, chloramine-T, $H_2O_2$/glacial acetic acid, and others. The reaction is performed at room temperature in aprotic or protic solvents, such as, for example, chlorinated hydrocarbons, such as dichloromethane, dichloroethane, chloroform, or lower aliphatic carboxylic acids, such as acetic acid, propionic acid, etc. The substitution is completed within a few minutes or several hours.

Another method for preparing the compounds of this invention involves performing in a manner known per se an exchange reaction of the iodine with radioactively labeled sodium-[I*] iodide, optionally in the presence of a catalyst, such as, for example, copper sulfate, in an inert protic or aprotic solvent, e.g., the solvents recited above. The halogen exchange is finished after several minutes or several hours. Also suitable are melts, for example in ammonium sulfate at an elevated temperature.

A further possibility for producing the compounds of general Formula I resides in reacting silylated ergoline derivatives with labeled iodine. For example, the 2-silylergolines described in EP-A 160,842 or the 12- or 13-silylergolines disclosed in EP-A 220,129 can be reacted with iodine, optionally in the presence of an acid. Suitable solvents are aprotic solvents, e.g., chlorinated hydrocarbons, such as dichloromethane, dichloroethane and chloroform, or ethers, such as diethyl ether and tetrahydrofuran. The reaction takes place at temperatures of 0° C. to 40° C. and is generally finished after about 2 hours. Suitably, acids are added to the reaction as catalysts, such as, for example, organic acids, e.g., acetic acid, trichloroacetic acid, trifluoroacetic acid, or inorganic acids, such as phosphoric acid. The reactions can be performed under an inert gas, such as, for example, nitrogen or argon.

The compounds are purified by means of usual methods, for example by HPL chromatography.

The usual physiologically compatible acid addition salts can be obtained by reaction with the corresponding acids, for example, according to the processes described in EP-A 220,129, using inorganic acids, e.g., hydrochloric acid, nitric acid, phosphoric acid, sulfuric acid, hydrobromic acid, hydriodic acid, nitrous acid or phosphorous acid, or organic acids, such as, for example, aliphatic mono- or dicarboxylic acids, phenyl-substituted alkane-carboxylic acids, hydroxyalkanecarboxylic acids, or alkenedicarboxylic acids, aromatic acids or aliphatic or aromatic sulfonic acids. Physiologically acceptable salts of these acids are, therefore, e.g., the sulfate, pyrosulfate, bisulfate, sulfite, bisulfite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutyrate, caproate, heptanoate, propiolate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluene-sulfonate, chlorobenzenesulfonate, xylenesulfonate, phenylacetate, phenylpropionate, phenylbutyrate, citrate, lactate, β-hydroxybutyrate, glycolate, malate, tartrate, methanesulfonate, propanesulfonate, naphthalene-1-sulfonate or naphthalene-2-sulfonate.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

All of the starting compounds are known or can be produced analogously to known methods. See, e.g., EP-21206, EP-A 220 129, EP-A 160 842, and EP-56 358.

In the foregoing and in the following examples, all temperatures are set forth uncorrected in degrees Celsius and unless otherwise indicated, all parts and percentages are by weight.

The entire disclosure of all applications, patents and publications, if any, cited above and below are hereby incorporated by reference.

EXAMPLE 1

0.011 μmol of 2-iodolisuride is dissolved in 0.25 ml of acetone (p.a.) and heated for one hour with reflux under a protective gas in the presence of 370 MBq of sodium-[$^{131}$I] iodide, carrier-free. After cooling to ice bath temperature, 0.25 ml of methanol, 0.1 ml of water and 1 μg of sodium iodide are added. The solution is drawn through a mixed-bed ion exchanger, thus obtaining [2-$^{131}$I]-iodolisuride.

EXAMPLE 2

0.16 μmole of lisuride is dissolved in 50 μl of tetrahydrofuran, containing 1 μl of 0.5N hydrochloric acid and added to 370 MBq f sodium-[$^{125}$I] iodide (carrier-free) in 50 μl of water. To this reaction solution is added 35 μg (0.125 umol) of chloramine-T, dissolved in 5 μl of water. After 2 hours, the reaction solution is passed through a low-pressure column yielding [2-$^{125}$I]-iodolisuride.

EXAMPLE 3

0.013 μmol of 2-iodolisuride is dissolved in 0.25 ml of acetone (p.a.) and heated with reflux under a protective gas in the presence of 370 MBq of sodium-[$^{125}$I] iodide (carrier-free) and 1 μg of copper sulfate for 3 hours. After cooling to ice bath temperature, 0.25 ml of methanol, 0.1 ml of water and 1 μg of sodium iodide are added. The solution is drawn through a mixed-bed ion exchanger, thus obtained [2-$^{125}$I]-iodolisuride.

EXAMPLE 4

0.09 μmol of 3-(9,10-didehydro-6-methyl-2-trimethylsilyl-8α-eroglinyl)-1,1-diethylurea is dissolved in 0.1 ml of chloroform, 40 μg of trichloroacetic acid (0.2 μmol) and 400 MBq of $^{131}$iodine are added in four portions, and the mixture is stirred for two hours at room temperature. The mixture is passed through a low-pressure column, thus obtaining [2$^{131}$I]-iodolisuride.

EXAMPLE 5

Analogously to Example 4, 0.1 μmol of 1,1-diethyl-3-(6-methyl-13-trimethylsilyl-8α-ergolinyl)urea yields [13-$^{125}$I]-iodoterguride in the same way after chromatography.

1,1-Diethyl-3-(2-$^{123}$I-6-n-propyl-8α-ergolinyl)urea 1,1-Diethyl-3-(13-$^{131}$I-6-n-propyl-8α-ergolinyl)urea

[12-$^{131}$-I]-Iodolisuride 3-(9,10-Didehydro-2-$^{131}$I-6-n-propyl-8α-ergolinyl)-1,1-diethylurea.

Analogously, the correspondingly labeled compounds are obtained with $^{131}$, $^{122}$I, $^{123}$I, $^{124}$I, and $^{132}$I.

EXAMPLE 6

Preparation of a Solution 0.01 μmol of a compound of this invention can be dissolved in 5 ml of ethanol-propanediol-saline (2:6:92) solution.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 2-(radioactive iodo)ergoline of formula II

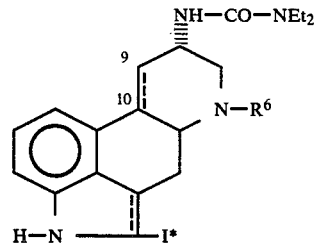

wherein

R$^6$ is a C$_1$–C$_6$ aliphatic hydrocarbon residue and

C$_2$–C$_3$ and

C$_9$–C$_{10}$ each independently represent a single or a double bond, or a pharmaceutically acceptable acid addition salt thereof.

2. A pharmaceutical composition comprising a compound of claim 1 and a pharmaceutically acceptable carrier.

3. 2-I*lisuride, a compound of claim 1.

4. A compound of claim 3, wherein I* is $^{125}$I or $^{131}$I.

5. A pharmaceutical composition comprising a compound of claim 3 and a pharmaceutically acceptable carrier.

6. A method of imaging monoamine receptors in tissue in vitro comprising contacting the tissue with a compound of claim 3 and subjecting the resultant tissue to a radioactive-iodine-sensitive imaging measurement.

7. A method of imaging monoamine receptors in a patient comprising administering to the patient a compound of claim 3 in a manner and amount effective to bind said monoamine receptors and subjecting the patient to a radioactive-iodine-sensitive imaging measurement.

8. A compound of claim 1, wherein the radioactive I is $^{121}$I, $^{122}$I, $^{123}$I, $^{124}$I, $^{125}$I, $^{131}$I or $^{132}$I isotope.

9. A compound of claim 8, wherein R$^6$ is alkyl or alkenyl.

10. A compound of claim 8, wherein R$^6$ is methyl.

11. A method of imaging monoamine receptors in tissue in vitro comprising contacting the tissue with a compound of claim 1 and subjecting the resultant tissue to a radioactive-iodine-sensitive imaging measurement.

12. A method of claim 11, wherein said receptors are dopamine receptors.

13. A method of imaging monoamine receptors in a patient comprising administering to the patient a compound of claim 1 in a manner and amount effective to bind said dopamine receptors and subjecting the patient to a radioactive-iodine-sensitive imaging measurement.

14. A method of claim 13, wherein said measurement is PET or SPECT.

15. A method of claim 13, wherein said receptors are dopamine receptors.

16. A 12- or 13-(radioactive iodo)ergoline of formula I

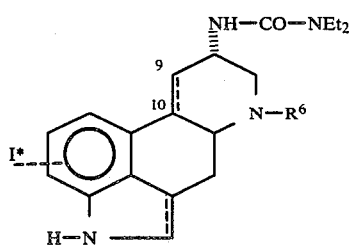

wherein
$R^6$ is a $C_{1-6}$ aliphatic hydrocarbon residue and $C_2-C_3$ and $C_9-C_{10}$ each independently represent a single or a double bond, wherein $I^*$ is in the 12- or 13-position, or a pharmaceutically acceptable acid addition salt thereof.

17. A pharmaceutical composition comprising a compound of claim 16 and a pharmaceutically acceptable carrier.

18. A compound of claim 16, wherein the radioactive I is $^{121}I$, $^{122}I$, $^{123}I$, $^{124}I$, $^{125}I$, $^{131}I$ or $^{132}I$ isotope.

19. A compound of claim 18, wherein the radioactive I is in the 12-position.

20. A compound of claim 18, wherein the radioactive I is in the 13-position.

21. A compound of claim 18, wherein $R^6$ is alkyl or alkenyl.

22. A compound of claim 18, wherein $R^6$ is methyl.

23. A compound of claim 18, wherein $C_2-C_3$ is a double bond.

24. A compound of claim 18, wherein $C_9-C_{10}$ is a double bond.

25. A method of imaging monoamine receptors in tissue in vitro comprising contacting the tissue with a compound of claim 16 and subjecting the resultant tissue to a radioactive-iodine-sensitive imaging measurement.

26. A method of claim 25, wherein said measurement is PET or SPECT.

27. A method of claim 25, wherein said receptors are dopamine receptors.

28. A method of imaging monoamine receptors in a patient comprising administering to the patient a compound of claim 16 in a manner and amount effective to bind said monoamine receptors and subjecting the patient to a radioactive-iodine-sensitive imaging measurement.

29. A method of claim 28, wherein said measurement is PET or SPECT.

30. A method of claim 28, wherein said receptors are dopamine receptors.

31. A method of imaging monoamine receptors in a patient comprising subjecting the patient to a radioactive-iodine-sensitive imaging measurement, said patient having been administered a compound of claim 16 in a manner and amount effective to bind said monoamine receptors.

* * * * *

UNITED STATES PATENT AND TRADEMARK OFFICE
CERTIFICATE OF CORRECTION

PATENT NO. : 4,857,298

DATED : August 15, 1989

INVENTOR(S) : WACHTEL ET AL

It is certified that error appears in the above-identified patent and that said Letters Patent is hereby corrected as shown below:

Column 6, line 3 of claim 1: reads "$C_2$-$C_3$ and"

should read --$C_2$====$C_3$ and --

Column 6, line 4 of claim 1:

reads "$C_9$-$C_{10}$ each independently represent a single or a"

should read --$C_9$====$C_{10}$ each independently represent a single or a --

Column 7, claim 16, line 14:

reads "$R^6$ is a $C_{1-6}$ aliphatic hydrocarbon residue and $C_2$-$C_3$"

should read -- $R^6$ is a $C_{1-6}$ aliphatic hydrocarbon residue and $C_2$====$C_3$ --

UNITED STATES PATENT AND TRADEMARK OFFICE
CERTIFICATE OF CORRECTION

PATENT NO. : 4,857,298

DATED : August 15, 1989

INVENTOR(S) : WACHTEL ET AL

It is certified that error appears in the above-identified patent and that said Letters Patent is hereby corrected as shown below:

Column 7, claim 16, line 15:

reads "and $C_9-C_{10}$ each independently represent a single"

should read -- and $C_9 = C_{10}$ each independently represent a single --

Column 8, claim 23, line 2:

reads "A compound of claim 18, wherein $C_2-C_3$ is a"

should read -- A compound of claim 18, wherein $C_2 = C_3$ is a --

Column 8, claim 24, line 4:

reads "A compound of claim 18, wherein $C_9-C_{10}$ is a"

should read -- A compound of claim 18, wherin $C_9 = C_{10}$ is a --

Signed and Sealed this

Tenth Day of July, 1990

Attest:

HARRY F. MANBECK, JR.

Attesting Officer     Commissioner of Patents and Trademarks

UNITED STATES PATENT AND TRADEMARK OFFICE
CERTIFICATE OF CORRECTION

PATENT NO. : 4,857,298

DATED : August 15, 1989

INVENTOR(S) : WACHTEL ET AL

It is certified that error appears in the above-identified patent and that said Letters Patent is hereby corrected as shown below:

Column 6, line 4 of claim 13:

reads "bind said dopamine receptors and subjecting the patient"

should read --bind said monoamine receptors and subjecting the patient"

Signed and Sealed this

Third Day of December, 1991

Attest:

HARRY F. MANBECK, JR.

*Attesting Officer*   *Commissioner of Patents and Trademarks*